United States Patent [19]

Holloman et al.

[11] Patent Number: 5,547,663

[45] Date of Patent: Aug. 20, 1996

[54] ABSOLUTE MOLECULAR WEIGHT POLYMERS AND METHODS FOR THEIR USE

[75] Inventors: Edward C. Holloman; Evan P. Kyba; Joon S. Park, all of Arlington, Tex.

[73] Assignee: Alcon Laboratories, Inc., Fort Worth, Tex.

[21] Appl. No.: 355,361

[22] Filed: Dec. 13, 1994

Related U.S. Application Data

[63] Continuation-in-part of Ser. No. 149,153, Nov. 8, 1993, abandoned, which is a continuation of Ser. No. 967,330, Oct. 28, 1992, abandoned, which is a continuation-in-part of Ser. No. 790,301, Nov. 8, 1991, abandoned.

[51] Int. Cl.$^6$ .......................... A61K 31/765; A61K 31/74
[52] U.S. Cl. ................... 424/78.04; 528/422; 424/78.37
[58] Field of Search ............................... 424/78.04, 78.37; 528/422

[56] References Cited

U.S. PATENT DOCUMENTS

| | | |
|---|---|---|
| 2,261,002 | 10/1941 | Ritter ..................................... 528/422 |
| 3,931,319 | 1/1976 | Green et al. . |
| 4,001,432 | 1/1977 | Green et al. . |
| 4,012,446 | 3/1977 | Green et al. . |
| 4,026,945 | 5/1977 | Green et al. . |
| 4,027,020 | 5/1977 | Green et al. . |
| 4,379,137 | 4/1983 | Ehlers et al. . |
| 4,395,541 | 7/1983 | Jacquet et al. . |
| 4,407,791 | 10/1983 | Stark . |
| 4,444,750 | 4/1984 | Green et al. . |
| 4,525,346 | 6/1985 | Stark . |
| 5,037,647 | 8/1991 | Chowhan et al. . |

FOREIGN PATENT DOCUMENTS 536017  8/1941  United Kingdom .

OTHER PUBLICATIONS

Grant et al., *Grant & Hackh's Chemical Dictionary*, Fifth Edition, McGraw–Hill, New York:1987, p. 462.
P. J. Flory, *Principles of Polymer Chemistry*, Cornell University Press, Ithaca:1953, Chapter II, pp. 29–68, and Chapter VIII, pp. 317–346.
Bailey et al., *J. Am. Chem. Soc.*, 77:165 (1955).
Biel et al., *J. Am. Chem. Soc.*, 79:6184 (1957).
Willette et al., *J. Med. Chem.*, 15:110 (1972).
Olomucki et al., *C. R. Acad. Sci.*, 237:192 (1953).
Bates et al., *J. Chem. Soc.*, 1854 (1954).
Nelson et al., *J. Med. Chem.*, 16:506 (1973).
Carothers, *J. Am. Chem. Soc.*, 51:2548 (1929).

*Primary Examiner*—Peter F. Kulkosky
*Attorney, Agent, or Firm*—Sally Yeager

[57] ABSTRACT

A process for preparing defined molecular weight polymers, particularly polyquaternary ammonium compounds, is disclosed. As the molecular weights of these compounds can be absolutely defined, rather than defined merely in terms of "number average molecular weight," these compounds are particularly useful as identification standards for other polymers which are made using conventional polymerization processes. The polyquaternary ammonium compounds described are further suitable for use as antimicrobial agents, particularly in ophthalmic compositions.

23 Claims, No Drawings

ABSOLUTE MOLECULAR WEIGHT POLYMERS AND METHODS FOR THEIR USE

CROSS REFERENCE TO RELATED APPLICATIONS

The present application is a continuation-in-part of U.S. patent application Ser. No. 08/149,153 filed Nov. 8, 1993 (abandoned), which is a continuation of U.S. patent application Ser. No. 07/967,330 (abandoned), filed Oct. 28, 1992, which is a continuation-in-part of U.S. patent application Ser. No. 07/790,301 filed Nov. 8, 1991 (abandoned).

BACKGROUND OF THE INVENTION

The present invention relates generally to polymers with an absolute molecular weight, particularly ionene-type polymers. The present invention also relates to methods for the use of such absolute molecular weight polymers, especially as identification standards to determine the molecular weight of ionene polymers and as antimicrobial agents.

The term "polymer" is generally defined as:

A substance composed of very large molecules consisting essentially of recurring long chain structural units that distinguish polymers from other types of organic molecules . . .

Grant et al., *Grant & Hackh's Chemical Dictionary, Fifth Edition*, McGraw-Hill, New York:1987, page 462 (emphasis added). In addition, polymers (especially high molecular weight polymers) often exhibit characteristic properties, such as high viscosity, long-range elasticity and high strength.

Although there are a wide variety of polymer structures, polymers may be generally expressed as combinations of a limited number of different structural units. In many instances, a single type of structural unit is present. These structural units may be connected in any of a number of ways to form different types of polymers, which may be referred to as either linear or non-linear (branched). In linear polymers, the structural units are connected to one another in a linear sequence, such as depicted below:

$$A'\text{-}A\text{-}A\text{-}A\text{-}A\text{-}A\text{-}A\text{-}A\text{-}A'' \text{ or } A'\text{-}(A\text{-})_{x-2}A''$$

where the termini, A' and A", may or may not be identical, but neither may be identical to A, the repeating structural unit, and x represents the degree of polymerization. On the other hand, in non-linear, or branched, polymers, the structural units are connected in non-linear or branched fashion, such as depicted below:

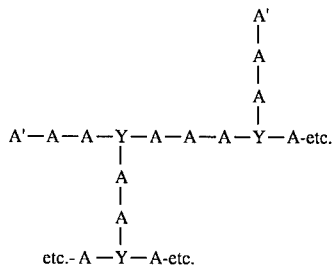

In fact, such branched structures may interconnect further to yield network structures, analogous to the spatial structures of graphite (planar network) or diamond (space network).

The degree of polymerization, represented by x, is an expression of the number of structural units in a given polymer molecule; however, this x becomes ambiguous when applied to an actual sample of polymeric material, since all of the polymer molecules in a given sample will not have the same value of x. In fact, the degree of polymerization in a given sample of polymeric material will vary over a considerable range, and the term "average degree of polymerization" is often used instead. The average degree of polymerization is obtained by dividing the total number of structural units by the total number of molecules. In similar manner, the molecular weight of a sample of polymeric material is also ambiguous; therefore, the terms "number average molecular weight"($M_n$) and "weight average molecular weight" ($M_w$) are generally used. The number average molecular weight of a sample of polymeric material represents the mass of the sample divided by the number of moles it contains. In contrast, the weight average molecular weight can be represented by the equation:

$$M_w = \Sigma W_x M_x$$

wherein $w_x$ is the weight-fraction of molecules whose weight is $M_x$.

A general discussion of polymers may be found in a treatise by P. J. Flory (*Principles of Polymer Chemistry*, Cornell University Press, Ithaca: 1953) especially Chapter II, pages 29–68, and Chapter VIII, pages 317–346.

Average molecular weight estimations of these types of polymeric ionene materials have been performed by gel permeation chromatography, vapor pressure osmometry, etc., but none of these methods are reliable in estimating the molecular weight, and the determinations are dependent on other variables, such as the particular internal standards used and the purity of the polymeric material. Thus, the absolute molecular weight compounds of this invention should shed light on the characterizations of ionene-type polymeric materials, especially with regard to the estimation of molecular weight.

For purposes of this specification, the polymerization reactions, such as are described above, which produce polymers of varying sizes will be generically referred to as "conventional polymerization processes."

SUMMARY OF THE INVENTION

The present invention relates to polymers with an absolute molecular weight, particularly ionene-type polymers. As used herein, the term "polymer" (or "polymers") will mean long chain compounds which have repeating subunits, regardless of whether the compounds can be identified with a specific molecular weight, or whether the compounds can only be identified with a number average molecular weight. In addition, the term "absolute molecular weight" will refer to molecular weights which can be calculated specifically, based on the standard atomic weights of the atomic constituents.

Because the absolute molecular weight of the compounds of the present invention can be determined, these compounds are particularly useful as identification standards for other polymers which are made using conventional polymerization processes. The polyquaternary ammonium compounds described are further suitable for use as antimicrobial agents, particularly in ophthalmic compositions.

The ophthalmic compositions of the present invention comprise the polymers of the present invention. These compositions include: contact lens care products, such as chemical disinfecting and storage solutions and preserved saline solutions; and other types of ophthalmic compositions, such as artificial tears and topical pharmaceutical preparations. For purposes of this specification, disinfectants and/or preservatives shall be collectively referred to as "antimicrobials" and compounds having disinfecting and/or preserving efficacy shall be referred to as compounds having "antimicrobial activity."

DETAILED DESCRIPTION OF THE INVENTION

The compounds of the present invention are polymers. They differ significantly from polymers made using conventional polymerization processes in that they have an absolute molecular weight, that is, the repeating unit is always the same rather than varying in number from which an average degree of polymerization can be calculated. The compounds of the present invention cannot be obtained by separation techniques performed on polymers made using conventional polymerization techniques.

The compounds of the present invention are those of structure:

$$W\text{-}BT(A\text{-}BT)_n\text{-}Y \qquad (I)$$

wherein:

W and Y are chosen to be the same or different, and are selected from OH, $NR^1R^2$, or $N^+R^1R^2R^3(Z^{31})$;

$R^{1\text{-}3}$ may be the same or different and are selected from: $CH_3$ and $C_2$–$C_{24}$ primary, secondary or tertiary alkyl or cycloalkyl groups; $C_3$–$C_{24}$ unsaturated hydrocarbon groups, including straight and branched chain alkenes; unsubstituted and variously substituted benzyl groups, particularly alkylated benzyl groups, where the alkyl group is as defined above;

BT is any pair of methylene units linked by a connector, such as the 1,2-, 1,3- and 1,4-phenylenes, and is preferably the trans-1,4-but-2-enylidene spacer;

A is $R^1R^2N^+Z^-$;

$Z^-$ is the anion corresponding to a variety of pharmaceutically acceptable Brønsted acids; e.g., $Br^-$, $I^-$, $Cl^-$, $H_2PO_4^-$, $MeCO_2^-$ and $Me_3CCO_2^-$; and n is an integer between 15 and 31.

Preferred compounds of the present invention are those of structure:

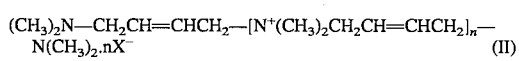

$$(CH_3)_2N\text{—}CH_2CH\text{=}CHCH_2\text{—}[N^+(CH_3)_2CH_2CH\text{=}CHCH_2]_n\text{—}N(CH_3)_2.nX^- \qquad (II)$$

wherein:

$X^-$ is a pharmaceutically acceptable anion, preferably a halide, particularly chloride; and n is an integer between 15 and 31.

It is preferred that, in the polymers of structures (I) and (II), n is an integer between 19 and 23.

There are two key steps in the synthesis of the absolute molecular weight polyquaternary ammonium compounds of the present invention: 1) the preparation of "base" materials containing identical reactive end groups, either as nucleophiles or as electrophiles; and 2) synthesis of the building blocks for elongation of the polymeric "base" units. The requirements of the building blocks are that: 1) they contain only one reactive end group which can interact with the "base" material; and 2) the non-reactive end group (e.g., allylic alcohol) is readily convertible to the corresponding reactive species for reaction with "base" material.

As illustrated in Scheme 1 and Scheme 2, below, quaternary ammonium homologues, such as 4, 7, 13, and 16, represent "base" materials. Synthesis of these materials are illustrated in equations 2, 4, 6, 8 and 10. The following abbreviations are used in the equations of Schemes 1 and 2: Me=$CH_3$; BT=trans—$CH_2$—CH=CH—$CH_2$; A=$Me_2N^+$ $Cl^-$; G=an alcohol protecting group, especially —C(O)($CH_2$)$_4CH_3$.

SCHEME 1

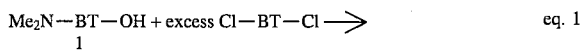
eq. 1

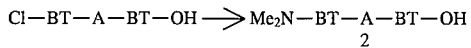

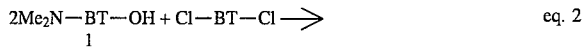
eq. 2

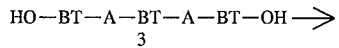

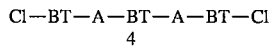

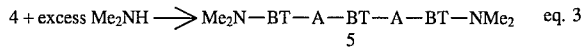
eq. 3

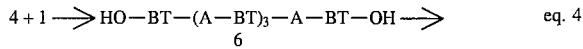
eq. 4

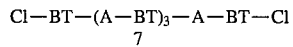

eq. 5

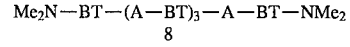

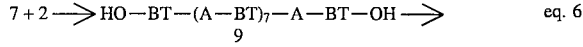
eq. 6

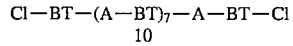

eq. 7

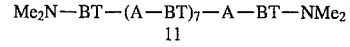

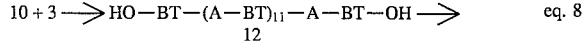
eq. 8

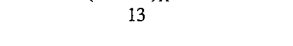

eq. 9

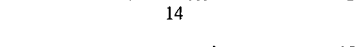

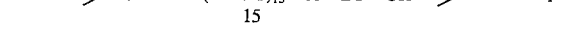
eq. 10

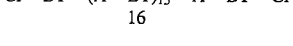

eq. 11

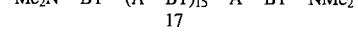

SCHEME 2

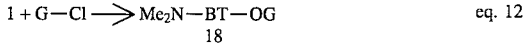
eq. 12

-continued
SCHEME 2

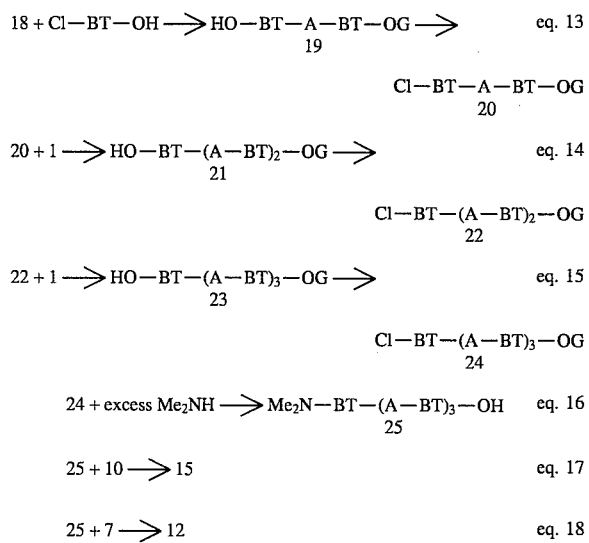

For the building block compounds, three compounds (1, 2 and 25) were utilized, although others could be used similarly. As is apparent, the number of quaternary ammonium functionalities in the "base" materials are increased by two, four and eight units, respectively, upon reaction with a "base"dichloride. Syntheses of these building block compounds are shown in eq.1 and eq.12–16. Building block compound, 1 is synthesized by following published procedures, and that of 2 is accomplished by treating 1 with an excess amount of 1,4-dichloro-2-butene, isolating the product, then reacting it with N,N-dimethylamine to afford 2. For synthesis of 25, 1 is blocked with ester (e.g., hexanoate) which is fairly stable under chlorination with thionyl chloride. This compound can be deblocked without much difficulty either by hydrolysis (acid or base) or aminolysis. 18 is reacted with 1-chloro-4-hydroxy-2-butene to yield the alcohol, 19, which is then converted to the corresponding chlorine compound, 20. This compound can be reacted with 1 to yield 21. This same procedure of chlorination and amination is repeated to afford 24. This is reacted with an excess amount of N,N-dimethylamine to aminolyze as well as aminate to afford 25. In the alternative, 25 can be synthesized by reacting 2 with 20 to afford 24 which can be readily converted to 25.

The procedure for synthesizing higher molecular weight polymer "base" material containing dihydroxy end groups involves the reaction between "base" material containing dichloro end groups and one of the building block compounds. For example, "base" 7 is reacted with building block 2 to yield 9 which has four more A-BT units in the molecule. This is well explained in eq. 6. Another example is illustrated in eq. 18, wherein, "base" material 7 is elongated by 8 units of A-BT with 25 as a building block compound.

Conversion of diallylic alcohol is readily accomplished by treatment with thionyl chloride for the lower molecular weight homologues but it is necessary to utilize concentrated hydrochloric acid for the higher homologues because of their limited solubility in thionyl chloride. Surprisingly, this class of polyquaternary ammonium compounds are stable under the latter chlorination condition (about 100° C. for 24 hours). Chlorinated allylic compounds were treated with N,N-dimethylamine to yield the corresponding tertiary amine containing polyquaternary ammonium compound.

In the examples below, the following standard abbreviations are used: g=grams (mg=milligrams); mol=moles (mmol=millimoles); mL=milliliters; mm Hg=millimeters of mercury; bp=boiling point (°C). All temperatures are reported as °C, unless otherwise stated. In addition, "NMR" refers to nuclear magnetic resonance spectroscopy, and "GC" refers to gas chromatography. The following references are also cited in the examples below by number: 1) Bailey, W. J. and E. Fujiwara, *J. Am. Chem. Soc.*, 77:165 (1955); 2) Biel, J. H. et al., *J. Am. Chem. Soc.*, 79:6184 (1957); 3) Willette, R. E. and R. C. Driscoll, *J. Med. Chem.*, 15:110 (1972); 4) Olomucki, M., *C. R. Acad. Sci.*, 237:192 (1953); 5) Bates, E. B. et al., *J. Chem. Soc.*, 1854 (1954); 6) Nelson, W. L. et al., *J. Med. Chem.*, 16:506 (1973).

EXAMPLE 1

Synthesis of 4-chloro-2-butyne-1-ol

Following published literature procedures[1], 4-chloro-2-butyne-1-ol was synthesized using 104.4 g (1.21 mol) of 2-butyne-1,4-diol, 105.5 g (1.33 mol) of pyridine and 158.6 g (1.33 mol) of thionyl chloride in dry chloroform. After washing the reaction mixture with cold water (1×100 mL) and separating the chloroform layer, the aqueous layer was extracted with chloroform (3×100 mL). All chloroform layers were combined and washed with cold saturated sodium bicarbonate (1×100 mL) followed with cold water, and then dried. Distillation of the residue trader reduced pressure afforded 47.2 g (37% yield) of 4-chloro-2-butyne-1-ol (bp 75°, 1.5 mm Hg; lit.[1]50°, 0.5 mm Hg). The structure was confirmed by $^1$H NMR. GC indicated a purity of 98%.

EXAMPLE 2

Synthesis of 4-dimethylamino-2-butyne-1-ol

Following published literature procedures[2], 4-dimethylamino-2-butyne-1-ol was prepared using 20.3 g (0.194 mol) of 4-chloro-2-butyne-1-ol and excess N,N-dimethylamine in tetrahydrofuran (THF). The reaction mixture was filtered and the filter cake washed with THF. The residue from the filtrates was distilled under reduced pressure to give 9.1 g (41% yield) of the aminoalcohol (bp 72°, 0.3 mm Hg). $^1$H NMR confirmed the structure, and purity was >99% by GC.

EXAMPLE 3

Synthesis of 1

Following published literature procedures[3], 1 was prepared by the reduction of 9.1 g (80.4 mmol) of 4-dimethylamino-2-butyne-1-ol with lithium aluminum hydride. The residue of the reaction filtrates was distilled under reduced pressure to give 7.2 g (78% yield) of the trans product (bp 63°, 0.4 mm; lit.[3,4] 50°–52.5°, 0.35 mm; 73°, 2.0 mm). The structure was confirmed by $^1$H NMR and $^{13}$C NMR, and purity was >99% by GC.

EXAMPLE 4

Synthesis of trans-2-butene-1,4-diol

Following published literature procedures[3,5], trans-2-butene-1,4-diol was prepared by the reduction of 22.2 g (0.26 mol) of 2-butyne-1,4-diol using lithium aluminum hydride in THF. After quenching the reaction, the reaction mixture was filtered and the filter cake washed with THF. The filtrate residue was distilled under reduced pressure to give 14 g (62% yield) of the trans diol (bp 95°, 0.4 mm). The structure was confirmed by $^1$H NMR, and purity by GC was 94%.

EXAMPLE 5

Synthesis of trans-4-chloro-2-butene-1-ol

Using a procedure[6] similar to that for the synthesis of 4-chloro-2-butyne-1-ol (Example 1), trans-4-chloro-2-butene-1-ol was prepared using 11.4 g (0.13 mol) of trans-2-butene-1,4-diol, 11.3 g (0.143 mol) of pyridine and 16.9 g (0.142 mol) of thionyl chloride in chloroform. Distillation under reduced pressure gave 3.43 g (25% yield) of the trans product (bp 55°–57°, 0.5 mm Hg; lit.[6] 50°–51°, 0.2–0.3 mm Hg). The structure was confirmed by $^1$H NMR, and purity by GC was 83%.

EXAMPLE 6

Synthesis of 3

3 was prepared by reacting 6.8 g (0.59 mol) of 1 and 3.5 g (0.28 mol) of trans-1,4-dichloro-2-butene in 50 mL of isopropanol at 85° for 5 hours. The product diol was recrystallized from ethyl acetate and ethanol and the crystals filtered and washed with ethyl acetate to give 7.19 g (73% yield) of white crystals.

$^1$H NMR (D$_2$O): δ6.31–6.14 (m, 4H, C=C(H)), 5.89–5.71 (m, 2H, C=C(H)CH$_2$OH), 4.12 (d, 4H, CH$_2$OH), 3.94 (d, 4H, =C(H)CH$_2$), 3.86 (d, 4H, =C(H)CH$_2$), 2.95 (s, 12H, N$^+$(CH$_3$)).

$^{13}$C NMR (D$_2$O): δ146.58 (s, 2 C,=C(H)CH$_2$OH), 132.48 (s, 2 C, N$^+$CH$_2$(H)C=C(H)CH$_2$N$^+$), 118.51 (s, 2 C, C=C(H)CH$_2$N$^+$), 68.18, 66.83 (2 s, 4 C, C=C(H)CH$_2$N$^+$), 63.57 (s, 2 C, =C(H)CH$_2$OH), 52.33 (s, 4 C, N$^+$(CH$_3$)).

Anal. Calcd. for C$_{16}$H$_{32}$Cl$_2$N$_2$O$_2$: C, 54.08; H, 9.08; N, 7.88. Found: C, 53.95; H, 9.03; N, 7.83.

EXAMPLE 7

Synthesis of 6

6 was prepared from 1 and 4.

4 was prepared by dissolving 3.1 g (8.7 mmol) of 3 in thionyl chloride at room temperature and stirring for 1 hour. Precipitation with ether followed sequentially by dissolution in ethanol and reprecipitation with ether gave 3.26 g (95% yield) of the dichloro product. The structure was confirmed by $^1$H NMR and $^{13}$C NMR.

6 was obtained by reacting 2.1 g (5.3 mmol) of 4, 1.3 g (10.9 mmol) of 1 and 0.08 g (0.62 mmol) of diisopropylethylamine in isopropanol at 85° for 5 hours. Evaporation of isopropanol and precipitation with acetone from ethanol (×3) gave 2.6 g (79% yield) of 6.

$^1$H NMR (D$_2$O): δ6.45–6.20 (m, 8H, C=C(H)CH$_2$N$^+$), 5.92–5.78 (m, 2H, C=C(H)CH$_2$OH), 4.19, 4.09, 4.03, 3.92 (4 d, 20H, C=C(H)CH$_2$), 3.08, 3.03 (2 s, 24H, N$^+$(CH$_3$)).

$^{13}$C NMR (D$_2$O): δ146.65 (s, 2 C, C=C(H)CH$_2$OH), 133.08, 132.65, 132.12 (3 s, 6 C, N$^+$CH$_2$(H)C=C(H)CH$_2$N$^+$), 118.52 (s, 2 C, C=C(H)CH$_2$N$^+$), 68.27, 67.65, 66.85 (3 s, 8 C, C=C(H)CH$_2$N$^+$), 63.60, (s, 2 C, C=C(H)CH$_2$OH), 52.7, 52.37 (2 s, 8 C, N$^+$(CH$_3$)).

EXAMPLE 8

Synthesis of 8

8 was prepared from 7 and N,N-dimethylamine.

The dichloro compound (7) was prepared by dissolving 3.9 g (6.3 mmol) of 6 in thionyl chloride at room temperature and stirring for 1 hour. Precipitation with ether, followed sequentially by dissolution in ethanol, and reprecipitation with ether gave 3.87 g (93% yield) of the dichloro product. The structure was confirmed by $^1$H NMR and $^{13}$C NMR.

8 was obtained by reacting 0.82 g (1.24 mmol) of 7 and 0.7 g (15.5 mmol) of aqueous N,N-dimethylamine for 2 hours at room temperature. Sodium bicarbonate was added to the reaction mixture, which was then stirred for 30 minutes in an ice bath. The sodium bicarbonate was precipitated with ethanol and filtered (×2). After evaporation of the ethanol from the filtrate, the reaction product was redissolved in ethanol and then precipitated with acetone (×2) to give 0.53 g (63% yield) of the diamine.

$^1$H NMR (D$_2$O): δ6.45–5.85 (m, 10H, C=C(H)), 4.10, 4.07, 4.06 (12H, N$^+$CH$_2$(H)C=C(H)CH$_2$N$^+$), 3.98 (d, 4H, N$^+$CH$_2$(H)C=C(H)CH$_2$N(CH$_3$)$_2$), 3.26 (d, 4H, C=C(H)CH$_2$N(CH$_3$)$_2$), 3.08, 3.04 (2 s, 24H, N$^+$(CH$_3$)), 2.32 (s, 12H, CH$_2$N(CH$_3$)$_2$).

$^{13}$C NMR (D$_2$O): δ142.18 (s, 2 C, C=C(H)CH$_2$N$^+$), 132.97, 132.67, 132.25 (3 s, 6 C, N$^+$CH$_2$(H)C=C(H)CH$_2$N$^+$), 123.99 (s, 2 C, C=C(H)CH$_2$N(CH$_3$)$_2$), 68.30, 67.69, 67.08 (3 s, 8 C, =C(H)CH$_2$N$^+$), 61.82 (s, 2 C, =C(H)CH$_2$N(CH$_3$)$_2$), 52.68, 52.45 (2 s, 8 C, N$^+$(CH$_3$)), 46.04 (s, 4 C, CH$_2$N(CH$_3$)).

EXAMPLE 9

Synthesis of 9

9 was prepared by reacting 1.06 g (1.61 mmol) of 7 with 0.86 g (3.46 mmol) of 2 and several drops of diisopropylethylamine in ethanol for 15 hours at room temperature, then for 2 hours at 50°. After evaporation of ethanol, the reaction mixture was redissolved in cold water and stirred with sodium bicarbonate for 30 minutes in an ice bath. The mixture was then precipitated with isopropanol and decanted. Methanol was then added to precipitate the sodium bicarbonate, and the methanol layer decanted and filtered. Methanol was evaporated from the filtrate and the residue acidified with 1N HCl. Precipitation of this solution with acetone gave 1.46 g (78% yield) of the diol.

$^1$H NMR (D$_2$O): δ6.45–6.18 (m, 16H, =C(H)CH$_2$N$^+$), 5.95–5.77 (m, 2H, =C(H)CH$_2$OH), 4.21,(d, 4H, =C(H)CH$_2$OH), 4.11, 4.05, 4.04, 4.03 (28H, N$^+$CH$_2$(H)C=C(H)CH$_2$N$^+$), 3.90 (d, 4H, =C(H)CH$_2$N$^+$), 3.08, 3.03 (2 S, 48H, N$^+$(CH$_3$)).

EXAMPLE 10

Synthesis of 12

12 was prepared by reacting 0.53 g (0.8 mmol) of 7 with 0.90 g (1.74 mmol) of Compound 26 and several drops of diisopropylethylamine in methanol for 15 hours at room temperature, then for 2 hours at 50°. After evaporation of methanol, the reaction mixture was redissolved in cold water and stirred with sodium bicarbonate for 30 minutes in an ice bath. The mixture was precipitated with isopropanol and decanted. Methanol was then added to precipitate the sodium bicarbonate, and the methanol layer decanted and filtered. Methanol was evaporated from the filtrate and the residue acidified with 1N HCl. Precipitation of this solution with acetone gave 1.1 g (81% yield) of the diol.

$^1$H NMR (D$_2$O) δ6.45–6.20 (m, 24H, =C(H)CH$_2$N$^+$), 5.95–5.77 (m, 2H, =C(H)CH$_2$OH), 4.18 (d, 4H, =C(H)CH$_2$OH), 4.11, 4.05, 4.04, 4.03 (44H, N$^+$CH$_2$(H)C=C(H)CH$_2$N$^+$), 3.08, 3.03 (2 S, 72H, N$^+$(CH$_3$)).

EXAMPLE 11

Synthesis of 14

14 was prepared from 13 and N,N-dimethylamine.

The dichloro compound (13) was prepared by dissolving 0.12 g (0.05 mmol) of 12 in thionyl chloride and stirring overnight at 50°. Precipitation with ether followed sequentially by dissolution in cold methanol and reprecipitation with ether and then acetone gave 0.05 g (54%) of the dichloro product. The structure was confirmed by $^1$H NMR and $^{13}$C NMR.

14 was obtained by reacting 0.05 g (0.03 mmol) of 13 and 0.04 g (0.89 mmol) of aqueous N,N-dimethylamine for 5 hours at room temperature. The product was precipitated with isopropanol, redissolved in water and reprecipitated with isopropanol (×2). The precipitate was redissolved in water and acidified with 1$\underline{\text{N}}$ HCl and precipitated twice from water with acetone to give 0.04 g (80% yield) of the diamine.

$^1$H NMR (D$_2$O): δ6.44–6.20 (m, 26H, C=C(H)), 4.11, 3.88, (52H, N$^+$C$\underline{\text{H}}_2$(H)C=C(H)C$\underline{\text{H}}_2$N$^+$), 3.07, (s, 72H, N$^+$(CH$_3$)), 2.86 (s, 12H, CH$_2$N(C$\underline{\text{H}}_3$)$_2$).

EXAMPLE 12

Synthesis of 15

15 was prepared by reacting 0.59 g (0.5 mmol) of 10 (prepared in a manner similar to the preparation of 4 and 7) with 0.58 g (1.12 mmol) of 25 and several drops of diisopropylethylamine in methanol for 15 hours at room temperature then for 2 hours at 50°. After evaporation of methanol, the reaction mixture was redissolved in cold water and stirred with sodium bicarbonate for 30 minutes in an ice bath. The mixture was precipitated with isopropanol and decanted. Methanol was then added to precipitate the sodium bicarbonate, and the methanol layer decanted and filtered. Methanol was evaporated from the filtrate and the residue acidified with 1$\underline{\text{N}}$ HCl. Precipitation of this solution with acetone gave 0.83 g (75% yield) of the diol.

$^1$NMR (D$_2$): δ6.47–6.19 (m, 32H, =C($\underline{\text{H}}$)CH$_2$N$^+$), 5.95–5.75 (m, 2H, =C($\underline{\text{H}}$)CH$_2$OH), 4.18 (d, 4H, =C(H)C$\underline{\text{H}}_2$OH), 4.12 (60H, N$^+$C$\underline{\text{H}}_2$(H)C=C(H)C$\underline{\text{H}}_2$N$^+$), 3.90 (d, 4H, =C(H)C$\underline{\text{H}}_2$N$^+$), 3.09, 3.04 (2 s, 96H, N$^+$(CH$_3$)).

EXAMPLE 13

Synthesis of 17

17 was prepared from 16 and N,N-dimethylamine.

The dichloro compound (16) was prepared by dissolving 0.12 g (0.054 mmol) of 15 in thionyl chloride and stirring overnight at 50°. Precipitation with ether, followed by dissolution in cold methanol and reprecipitation first with ether and then with acetone gave 0.07 g (58% yield) of the dichloro product. The structure was confirmed by $^1$H NMR and $^{13}$C NMR.

17 was obtained by reacting 0.07 g (0.031 mmol) of 16 and 0.06 g (1.33 mmol) of aqueous N,N-dimethylamine for 5 hours at room temperature. The product was precipitated with isopropanol, redissolved in water and reprecipitated with isopropanol (×2). The precipitate was redissolved in water and acidified with 1$\underline{\text{N}}$ HCl and precipitated twice from water with acetone to give 0.05 g (71% yield) of the diamine.

$^1$H NMR (D$_2$O): δ6.44–6.20 (m, 34H, C=C(H)), 4.11, 3.88, (68H, N$^+$C$\underline{\text{H}}_2$(H)C=C(H)C$\underline{\text{H}}_2$N$^+$), 3.07, (s, 96H, N$^+$ (CH$_3$)), 2.86 (s, 12H, CH$_2$N(C$\underline{\text{H}}_3$)$_2$).

EXAMPLE 14

Synthesis of 25

25 was prepared from the following reactions (a)–(e).

(a) Preparation of 18

Hexanoyl chloride in chloroform (2.52 g, 18.7 mmol) was added to a stirred chloroform solution of 2.18 g (18.9 mmol) of 1 and 1.90 g (18.8 mmol) of triethylamine in an ice bath. Upon addition of the hexanoyl chloride, the mixture was allowed to react (with stirring) at room temperature overnight. Saturated sodium bicarbonate solution (50 mL) was then added to the reaction mixture and the mixture stirred for 1 hour. The chloroform layer was then separated and washed first with saturated sodium bicarbonate solution (1×50 mL), then with saturated sodium chloride solution (2×50 mL). The organic layer was dried over magnesium sulfate, filtered, and the chloroform evaporated. The residue was distilled under reduced pressure to give 2.77 g (69%) of 18 (bp 85°, 0.4 mm Hg). Structure was confirmed by $^1$H NMR and $^{13}$C NMR.

(b) Preparation of 19

19 was prepared by addition of 2.7 g (24 mmol) of trans-4-chloro-2-butene-1-ol to a solution of 5.0 g (25 mmol) of 18 and 0.5 g (3.5 mmol) of diisopropylethylamine in THF. The mixture was allowed to react for 3 hours at 60°, then the THF was evaporated and the residue redissolved in chloroform and precipitated with ether (×2). The precipitate was redissolved in 100 mL of cold chloroform and washed with cold aqueous HCl (pH=3.0) saturated with sodium chloride (2×50 mL) and then with cold saturated sodium chloride solution (1×25 mL). The chloroform layer was dried over magnesium sulfate, filtered, and the chloroform evaporated. The residue was redissolved in chloroform and precipitated with ether (×2) affording 7.34 g (97% yield) of 19.

$^1$H NMR (CDCl$_3$): δ6.43–6.25, 6.10–5.76 (2 m, 4H, C=C(H)), 4.67 (d, 2H, (O(COCH$_2$), 4.33 (d, 2H, N$^+$C$\underline{\text{H}}_2$(H)C=C(H)CH$_2$OH), 4.20, 4.15 (4H, C$\underline{\text{H}}_2$N$^+$CH$_2$(H)C=C(H)C$\underline{\text{H}}_2$OH), 3.23 (s, 6H, N$^+$(CH$_3$)), 2.34 (t, 2H, OC(O)CH$_2$), 1.62 (m, 2H, CH$_2$C$\underline{\text{H}}_2$C(O)), 1.33 (m, 4H, CH$_3$C$\underline{\text{H}}_2$C$\underline{\text{H}}_2$), 0.89 (t, 3H, CH$_2$C$\underline{\text{H}}_3$).

$^{13}$C NMR (CDCl$_3$): δ61.17 (s, 1 C, =C(H)C$\underline{\text{H}}_2$OH), 49.38 (s, 2 C, N$^+$(CH$_3$)).

(c) Preparation of 21

21 was prepared by reacting 20 with 1.

The chloro compound (20) was obtained by dissolving 2 g (6.3 mmol) of 19 in cold thionyl chloride in an ice bath. After dissolution, the reaction was stirred at room temperature for 2 hours, followed by precipitation with ether. The residue was dissolved in isopropanol and precipitated with ether (×2) to give 1.92 g (91% yield) of 20.

20 (1.9 g, 5.6 mmol) and 0.7 g (6.3 mmol) of 1 were dissolved in THF and heated at 60° for 1 hour. The upper layer was decanted and the precipitate that had formed washed with ether. The precipitate was redissolved in ethanol and precipitated with acetone to give 1.96 g (76% yield) of the product, 21.

$^1$H NMR (D$_2$): δ6.40–6.19 (m, 4H, C=C(H)), 6.05, 5.80 (m, 2H, N$^+$CH$_2$(H)C=C(H)CH$_2$OH), 4.72 (d, 2H, =C(H)C$\underline{\text{H}}_2$OC(O)), 4.21 (d, 2H, =C(H)C$\underline{\text{H}}_2$OC(O)), 4.04, 3.95 (2 d, 8H, =C(H)C$\underline{\text{H}}_2$N$^+$CH$_2$ (H)C=), 3.05 (s, 12H, N$^+$(CH$_3$)), 2.43 (t, 2H, OC(O)CH$_2$), 1.60 (m, 2H, CH$_2$C$\underline{\text{H}}_2$C(O)), 1.27 (m, 4H, CH$_3$C$\underline{\text{H}}_2$C$\underline{\text{H}}_2$), 0.85 (t, 3H, CH$_2$C$\underline{\text{H}}_3$).

$^{13}$C NMR (D$_2$O): δ3.32 (s, 1 C, =C(H)C$\underline{\text{H}}_2$OH).

Anal. Calcd. for C$_{22}$H$_{42}$Cl$_2$N$_2$O$_3$: C, 56.04; H, 9.41; N, 5.94. Found: C, 56.35; H, 9.22; N, 5.62.

(d) Preparation of 23

23 was prepared by reacting 22 with 1.

The chloro compound (22) was obtained by dissolving 0.43 g (0.95 mmol) of 21 in cold thionyl chloride in an ice bath. After dissolution, the reaction was stirred at room temperature for 2 hours, followed by precipitation with ether. The residue was dissolved in ethanol and precipitated with ether (×2) to give 0.4 g (93%) of the chlorinated product. Structure was confirmed by $^1$H NMR and $^{13}$C NMR.

22 (0.43 g, 0.95 mmol) and 0.13 g (1.1 mmol) of 1 were dissolved in N,N-dimethylacetamide and stirred for 3 hours at room temperature. Precipitation was completed by the addition of acetone to the reaction mixture. The upper layer was then decanted and the precipitate dissolved in cold water and stirred with sodium bicarbonate for 15 minutes in an ice bath. Sodium bicarbonate was precipitated with ethanol, the mixture filtered and ethanol evaporated. The residue was redissolved in water and precipitated with acetone to give 0.45 g (85% yield) of the product, 23.

$^1$H NMR (D$_2$O): δ6.48–5.73 (m, 8H, C=C(H)), 4.77 (d, 2H, =C(H)C$\underline{H}_2$OC(O)), 4.20, 4.11, 4.03, 3.96 (4 d, 14H, =C(H)C$\underline{H}_2$N$^+$ C$\underline{H}_2$ (H)C=), 3.13, 3.08 (2 s, 18H, N$^+$(CH$_3$)), 2.46 (t, 2H, OC(O)CH$_2$), 1.63 (m, 2H, CH$_2$C $\underline{H}_2$C(O)), 1.30 (m, 4H, CH$_3$C$\underline{H}_2$C$\underline{H}_2$), 0.88 (t, 3H, CH$_2$C $\underline{H}_3$).

(e) Preparation of 25

25 was prepared by reacting 24 with N,N-dimethylamine.

The chloro compound (24) was obtained by dissolving 2.6 g (4.4 mmol) of 23 in cold thionyl chloride and stirring in an ice bath until 23 was completely dissolved, after which the ice bath was removed and the reaction stirred for 1 hour at room temperature. The reaction product was precipitated with ether and the precipitate was dissolved in cold ethanol in an ice bath and then reprecipitated with ether (×2). The precipitate was then redissolved in cold water in an ice bath and precipitated again with acetone to give 3.6 g (5.9 mmol) of 24. Structure was confirmed by $^1$H NMR.

To 3.41 g (5.6 mmol) of 24 in an ice bath was added 2.4 g (53.2 mmol) of N,N-dimethylamine to dissolve the chloro compound. The reaction mixture was stirred at room temperature for 2 hours. Sodium bicarbonate was added and the mixture stirred for 30 minutes in an ice bath. The sodium bicarbonate was precipitated with ethanol and filtered and the ethanol evaporated, followed by redissolution in water and precipitated with acetone (×2) affording 2.91 g (59% yield) of 25.

$^1$H NMR (D$_2$O): δ6.41–5.78 (m, 8H, C=C(H)), 4.19, 4.10, 4.05, 3.93 (4 d, 16H, =C(H)C$\underline{H}_2$), 3.07, 3.03 (2 s, 18H, N$^+$(CH$_3$)), 2.20 (s, 6H, N(CH$_3$)$_2$).

The polymers of the present invention may be used as antimicrobials in ophthalmic compositions, particularly as disinfectants in contact lens care products and as preservatives in other types of ophthalmic compositions, such as artificial tears or topical pharmaceutical preparations. In general, the polymers of the present invention will be present in the compositions at a concentration between about 0.00001 and about 1.0 percent by weight (wt %). If used as a disinfectant, the polymers are preferably present at a concentration of between about 0.0005 and about 0.5 wt %; if used as a preservative, the polymers are present at a concentration between about 0.00005 and about 0.05 wt %. It is preferred that the polymers are present at a concentration of between about 0.001 and about 0.05 wt % if used as a disinfectant and between about 0.0001 and about 0.01 wt % if used as a preservative.

The ophthalmic compositions of the present invention may additionally contain other components, for example, ophthalmically acceptable buffers, tonicity agents, surfactants, and therapeutic agents.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A polymer, wherein the number of repeating units is constant, of the structure:

W-BT(A-BT)$_n$-Y wherein:

W and Y are chosen to be the same or different, and are selected from OH, NR$^1$R$^2$, or N$^+$R$^1$R$^2$R$^3$(Z$^-$);

R$^{1-3}$ may be the same or different and are selected from: CH$_3$ and C$_2$–C$_{24}$ primary, secondary or tertiary alkyl or cycloalkyl groups; C$_3$–C$_{24}$ unsaturated hydrocarbon groups, including straight and branched chain alkenes; unsubstituted and variously substituted benzyl groups, particularly alkylated benzyl groups, where the alkyl group is as defined above;

BT is any pair of methylene units linked by a connector;

A is R$^1$R$^2$N$^+$Z$^-$;

Z$^-$ is the anion corresponding to a variety of pharmaceutically acceptable Brønsted acids; and n is an integer between 15 and 31.

2. The polymer of claim 1, wherein n is an integer between 19 and 23.

3. The polymer of claim 1, wherein Z$^-$ is selected from the group consisting of: Br$^-$, I$^-$, Cl$^-$, H$_2$PO$_4^-$, MeCO$_2^-$, and Me$_3$CCO$_2^-$.

4. The polymer of claim 1, wherein BT is selected from the group consisting of: 1,2-, 1,3-, and 1,4-phenylenes, and trans-1,4-but-2-enylidene.

5. The polymer of claim 4, wherein BT is trans-1,4-but-2-enylidene.

6. A polymer, wherein the number of repeating units is constant, of the structure:

(CH$_3$)$_2$N—CH$_2$CH=CHCH$_2$—[N$^{+(CH_3)}_3$)$_2$CH$_2$CH=CHCH$_2$]$_n$—N(CH$_3$)$_2$.nX$^-$ wherein:

X$^-$ is a pharmaceutically acceptable anion; and n is an integer between from 15 and 31.

7. The polymer of claim 6, wherein X$^-$ is a halide.

8. The polymer of claim 7, wherein X$^-$ is chloride.

9. The polymer of claim 6, wherein n is an integer between 19 and 23.

10. A pharmaceutical composition comprising an antimicrobially effective amount of a polymer, wherein the number of repeating units is constant, of the structure:

W-BT(A-BT)$_n$-Y wherein:

W and Y are chosen to be the same or different, and are selected from OH, NR$^1$R$^2$, or N$^+$R$^1$R$^2$R$^3$(Z$^-$);

R$^{1-3}$ may be the same or different and are selected from: CH$_3$ and C$_2$–C$_{24}$ primary, secondary or tertiary alkyl or cycloalkyl groups; C$_3$–C$_{24}$ unsaturated hydrocarbon groups, including straight and branched chain alkenes; unsubstituted and variously substituted benzyl groups, particularly alkylated benzyl groups, where the alkyl group is as defined above;

BT is any pair of methylene units linked by a connector;

A is $R^1R^2N^+Z^-$;

$Z^-$ is the anion corresponding to a variety of pharmaceutically acceptable Brønsted acids; and n is an integer between 15 and 31;

and a pharmaceutically acceptable carrier.

11. The pharmaceutical composition of claim 10, wherein the polymer is present at a concentration between about 0.00001 and about 1.0 percent by weight.

12. The pharmaceutical composition of claim 10, wherein n is an integer between 19 and 23.

13. The pharmaceutical composition of claim 10, wherein $Z^-$ is selected from the group consisting of: $Br^-$, $I^-$, $Cl^-$, $H_2PO_4^-$, $MeCO_2^-$, and $Me_3CCO_2^-$.

14. The pharmaceutical composition of claim 10, wherein BT is selected from the group consisting of: 1,2-, 1,3- and 1,4-phenylenes, and trans-1,4-but-2-enylidene.

15. The pharmaceutical composition of claim 14, wherein BT is trans-1,4-but-2-enylidene.

16. A pharmaceutical composition comprising an antimicrobially effective amount of a polymer, wherein the number of repeating units is constant, of the structure:

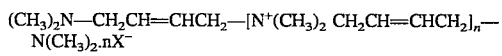

$(CH_3)_2N-CH_2CH=CHCH_2-[N^+(CH_3)_2\ CH_2CH=CHCH_2]_n-N(CH_3)_2 \cdot nX^-$ wherein:

$X^-$ is a pharmaceutically acceptable anion; and n is an integer between 15 and 31;

and a pharmaceutically acceptable carrier.

17. The pharmaceutical composition of claim 16, wherein the polymer is present at a concentration between about 0.00001 and about 21.0 percent by weight.

18. The pharmaceutical composition of claim 16, wherein $X^-$ is a halide.

19. The pharmaceutical composition of claim 18, wherein $X^-$ is chloride.

20. The pharmaceutical composition of claim 16, wherein n is an integer between 19 and 23.

21. A method for preserving an ophthalmic composition by using an antimicrobially effective amount of the polymer of claim 1.

22. A method for preserving an ophthalmic composition by using an antimicrobially effective amount of the polymer of claim 6.

23. A method for preserving an ophthalmic composition by using an antimicrobially effective amount of the polymer of claim 9.

* * * * *